(12) United States Patent
Pfirrmann et al.

(10) Patent No.: US 8,852,617 B2
(45) Date of Patent: Oct. 7, 2014

(54) ANTIMICROBIAL DENTAL CARE PREPARATION

(75) Inventors: Rolf W. Pfirrmann, Weggis (CH); Peter Geistlich, Stansstad (CH)

(73) Assignee: Geistlich Pharma AG, Wolhusen (CH)

( * ) Notice: Subject to any disclaimer, the term of this patent is extended or adjusted under 35 U.S.C. 154(b) by 0 days.

(21) Appl. No.: 13/876,097

(22) PCT Filed: Sep. 26, 2011

(86) PCT No.: PCT/IB2011/002255
§ 371 (c)(1),
(2), (4) Date: Mar. 26, 2013

(87) PCT Pub. No.: WO2012/042349
PCT Pub. Date: Apr. 5, 2012

(65) Prior Publication Data
US 2013/0189199 A1    Jul. 25, 2013

Related U.S. Application Data

(60) Provisional application No. 61/386,662, filed on Sep. 27, 2010.

(51) Int. Cl.
*A61K 8/49* (2006.01)
*A61K 8/21* (2006.01)
*A61Q 11/00* (2006.01)
*A61Q 17/00* (2006.01)

(52) U.S. Cl.
CPC . *A61K 8/49* (2013.01); *A61Q 11/00* (2013.01); *A61K 8/21* (2013.01); *A61Q 17/005* (2013.01)
USPC ........................................... 424/404; 424/52

(58) Field of Classification Search
CPC ..... A61J 7/0015; A61J 7/0023; A61J 7/0046; A61K 9/0056; A61K 9/1652; A61K 9/2081; A61K 31/167; A61K 31/192
USPC ...................................... 424/52, 54, 401, 485
See application file for complete search history.

(56) References Cited

U.S. PATENT DOCUMENTS

| | | | | |
|---|---|---|---|---|
| 3,070,510 | A * | 12/1962 | Broge et al. | 424/52 |
| 3,151,027 | A * | 9/1964 | Broge et al. | 424/401 |
| 3,423,408 | A | 1/1969 | Pfirrmann et al. | |
| 4,096,241 | A | 6/1978 | Geistlich et al. | |
| 4,473,547 | A * | 9/1984 | Sipos | 424/52 |
| 2003/0066753 | A1 | 4/2003 | Pfirrmann | |
| 2006/0140882 | A1* | 6/2006 | Tambs et al. | 424/53 |

FOREIGN PATENT DOCUMENTS

| | | |
|---|---|---|
| DE | 252972 A1 | 1/1988 |
| DE | 102009029164 A1 | 7/2010 |
| GB | 1550139 | 8/1979 |
| WO | 94/03174 A1 | 2/1994 |

OTHER PUBLICATIONS

H. R. Muehlemann et al.: "Inhibition of Plaque Growth with Taurolin, Vantocil and Amine Fluoride," Helvetica Odontologica Acta, vol. 19, No. 2, Jan. 1975, pp. 57-60, XP009156044.

* cited by examiner

*Primary Examiner* — Walter Webb
(74) *Attorney, Agent, or Firm* — Rothwell, Figg, Ernst & Manbeck, P.C.

(57) ABSTRACT

A dental care preparation in a form of a toothpaste or tooth gel dentifrice includes an antimicrobial amount of at least one antimicrobial N-methylol transfer agent, and at least one of a fluoride compound or a source of fluoride ions.

18 Claims, No Drawings

ANTIMICROBIAL DENTAL CARE PREPARATION

CROSS REFERENCE TO RELATED APPLICATIONS

This application is a 35 U.S.C. §371 National Phase Entry Application from PCT/IB2011/002255, filed Sep. 26, 2011, and designating the United States, which claims the benefit of U.S. Provisional Application No. 61/386,662 filed Sep. 27, 2010, which is incorporated herein in its entirety.

BACKGROUND OF THE INVENTION

1. Technical Field

This invention relates to antimicrobial dental care preparations.

2. Description of the Background Art

Oral compositions such as toothpastes, gels and mouth washes are designed to loosen and remove plaque in conjunction with a regular toothbrushing regimen, and typically include fluoride to prevent tooth decay. Dental plaque is present to some degree, in the form of a film, on virtually all dental surfaces. It is a byproduct of microbial growth, and comprises a dense microbial layer consisting of a mass of microorganisms embedded in a polysaccharide matrix. Plaque itself adheres thinly to dental surfaces and is removed only with difficulty even through a rigorous brushing regimen. Moreover, plaque rapidly reforms on the tooth surface after it is removed. Plaque may form on any part of the tooth surface, and is found particularly at the gingival margin, in cracks in the enamel, and on the surface of dental calculus. The danger associated with the formation of plaque on the teeth lies in the tendency of plaque to build up and eventually produce gingivitis, periodontitis and other types of periodontal disease, as well as dental caries and dental calculus.

Conventional treatments of plaque include antibacterial agents such as triclosan. Triclosan is known for inhibiting growths of microorganisms, especially bacteria. Because bacteria are components of plaque, triclosan may reduce plaque formation when it is effectively applied to the teeth. However, reports have suggested that triclosan has negative effects on humans and the environment.

Triclosan can be degraded by sunlight into a dioxin. Triclosan can also combine with chlorine in tap water to form chloroform gas, which the United States Environmental Protection Agency classifies as a probable human carcinogen. Experiments on Triclosan have demonstrated hazardous effects towards animals including liver, kidney and intestinal flora damage. Further, Triclosan accumulates in fatty tissue and passes into breast milk.

In certain toothpastes copolymers are added to increase the attachment to the gingiva. Thus the retention time of Triclosan in the oral cavity can be extended up to 12 hours. The retention time may add to the damage of the skin flora and may permanently damage the oral micro-flora.

Another disadvantage to Triclosan is the forming of a resistance. This occurs due to low concentrations and frequent use of Trisclosan. Cross resistance with frequently used antibiotics has also been observed and this may be a cause of antibiotic resistance.

Triclosan is also considered environmentally hazardous in water and is very difficult to degrade by biological means.

Taurolidine, taurultam, N-methylol taurinamide and the like are bactericidal compounds that do not exhibit the phenomenon of resistance due to their mechanism of action, which involves a cross-linking reaction with the cell wall of bacteria. Taurolidine is a synthetic derivative of the naturally occurring 2-aminoethane sulphonic acid, taurine. The use of taurolidine as a potential antimicrobial substance, acting by a methylol transfer mechanism, has been disclosed in GB 1,124,285. Taurolidine solution is sold by Ed. Geistlich Sohne AG. under the registered Trade Mark Taurolin®. The antibacterial substance taurultam is closely related to taurolidine and, indeed, is formed during the methylol transfer reaction between taurolidine and target substances. Taurultam is slightly more water soluble than taurolidine but possesses fewer methylol transfer groupings.

There continues to be a need for new formulations of an antimicrobial toothpaste.

SUMMARY OF THE INVENTION

In accordance with one embodiment, a dental care preparation in a form of a toothpaste or tooth gel dentifrice comprises an antimicrobial amount of at least one antimicrobial N-methylol transfer agent, and at least one of a fluoride compound or a source of fluoride ions.

DETAILED DESCRIPTION OF CERTAIN EMBODIMENTS

According to one embodiment, the present disclosure provides the use of taurolidine, taurultam, N-methylol taurinamide and the like in a preparation of an oral composition such as toothpaste or tooth gel dentifrice.

Certain embodiments of the disclosure provide a dental care preparation in the form of a toothpaste or a gel dentifrice comprising at least one antimicrobial N-methylol transfer agent or a derivative thereof and at least one of the a fluoride compound or a source of fluoride ions.

The N-methylol agent of the present disclosure may be dissolved in the preparation. The N-methylol agent may also be dispersed in the dental care preparation as a microcrystalline, crystalline, or a powder form. According to certain embodiments, the N-methylol agent is taurolidine, taurultam, 1183B (cyclo-taurolidine), N-methylol taurinamide or any combination thereof.

In certain embodiments, the preparation further comprises a source of zinc ions. A suitable source of zinc ions is a zinc salt such as zinc chloride, zinc citrate, zinc acetate, zinc sulphate, zinc gluconate, zinc salicylate, zinc lactate, zinc malate, zinc maleate, zinc tartate, zinc carbonate, zinc phosphate, zinc oxide or zinc sulphate.

Certain embodiments of the disclosure further comprise a thickening agent. The thickening agent may be, e.g., Irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose and sodium carboxymethyl cellulose or any combination thereof.

Certain embodiments of the disclosure further comprise a pH control agent. The pH control agent may be, e.g., sodium hydroxide.

Certain embodiments of the disclosure further comprise a humectant. The humectant may be, e.g., glycerine, sorbitol, an alkylene glycol, or any combination thereof.

Certain embodiments of the disclosure further comprise a sweetening agent. The sweetening agent may be, e.g., sucrose, lactose, maltose, xylitol, sodium cyclamate, perillartine, aspartyl phenyl alanine methyl ester, saccharine, or any combination thereof.

Certain embodiments of the disclosure further comprise a binding agent. The binding agent may be, e.g., polyvinylmethyl ether maleic acid copolymer.

Certain embodiments of the disclosure further comprise a hydrating agent. The hydrating agent may be, e.g., glycerin, polyethylene glycol, paraffin oil, or any combination thereof.

Certain embodiments of the disclosure further comprise a coloring agent. The coloring agent may be, e.g., titanium dioxide.

Certain embodiments of the disclosure further comprise a surfactant. The surfactant may be, e.g., sodium lauryl sulfate, sodium lauryl sarcoside, sodium monoglyceride sulfate, or any combination thereof.

N-methylol transfer agents have been shown to be antimicrobial. When an N-methylol transfer agent is part of a dental care preparation, according to certain embodiments, the preparation may reduce bacteria in the dental care preparation, and/or in the mouth. The dental care preparation of the present disclosure may contain an N-methylol transfer agent in solution, and/or in crystalline, microcrystalline and/or powder form.

N-methylol transfer agents include, e.g., taurolidine, taurultam, 1183B (cyclo-taurolidine), N-methylol taurinamide or any combination thereof. The compounds taurolidine and taurultam are disclosed in U.S. Pat. No. 5,210,083. Other suitable N-methylol-containing and N-methylol-transferring compounds include, e.g., taurin derivatives, taurinamide derivatives, urea derivatives, organic or inorganic salts thereof. Examples of derivatives of taurolidine, taurultam, taurinamide and urea useful in the present disclosure can be found in WO 01/39763A2. In certain embodiments, the N-methylol-containing and N-methylol-transferring agents for utilization in accordance with the present disclosure are taurolidine, taurultam, biologically active derivatives thereof and mixtures thereof.

Taurolidine (Bis-(1,1-dioxoperhydro-1,2,4-thiadiazinyl-4)methane) was developed by Geistlich Pharma. It is made up of two molecules of taurinamid and three molecules formaldehyde forming a two-ringed structure bridged by a methylene group.

Taurolidine has antimicrobial and anti-endotoxin effects. It acts by a chemical reaction, so no microorganism resistance has been observed as of yet. This effect of taurolidine is mediated by its active metabolites, which are donators of active methylol-groups: Methylol-Taurultam and Methylol-Taurinamide. The active methylol groups inactivate by reacting with the cell wall of bacteria and with the primary amino groups of endotoxins.

In certain embodiments of the present disclosure, a portion (e.g., up to 50% or more) of the taurolidine present in the toothpaste is taurolidine in solution, while a portion (e.g., up to 50% or more) is taurolidine in crystalline, micronized crystal and/or powder form.

In certain embodiments, the N-methylol transfer agent is at a concentration in the inventive preparation within a range of about 0.01% to about 10% by weight, within the range of about 0.1% to about 5% by weight, or within the range of about 1% to about 3% by weight, for example about 2% by weight. This may be included in a ratio of, e.g., 1:9, 2:8, 3:7, 4:6, 1:1, 6:4, 7:3, 8:2 or 9:1, and the like of N-methylol transfer agent in solution to N-methylol transfer agent in crystalline and/or powdered form respectively.

In one embodiment, about 3% N-methylol transfer agent in the dental care preparation is useful for treating people with active mouth infections.

Fluoride ions or fluoride compounds included in the dental care preparations of the present disclosure also may provide an anticavity effect. Among these materials are, e.g., inorganic fluoride salts, such as soluble alkali metal fluoride salts, for example, sodium fluoride, potassium fluoride, ammonium fluoride, sodium monofluorophosphate, sodium hexafluorosilicate or stannous fluoride.

The use of fluoride in a dental care preparation can help prevent tooth decay, inhibit loss of minerals from tooth enamel and encourage remineralization. Fluoride also adversely affects bacteria that cause cavities. As with conventional antibiotics, a resistance to the fluoride may occur. Due to taurolidine's antimicrobial and anti-endotoxin effects, the dental care preparation may act against fluoride resistant bacteria.

In certain embodiments, the combination of taurolidine and fluoride enhances the time duration of the antimicrobial effect of taurolidine.

Since activity of agents such as taurolidine and taurultam are dependent on transfer of an N-methylol group, it could not have been predicted that the presence of fluoride ions or compounds would not inactivate or prevent N-methylol transfer by said agents.

The amount of fluorine-providing salt may generally be present in the dental care preparation at a concentration of about 0.0005% to about 3.0% by weight. Any suitable minimum amount of such salt may be used, but it is preferable to employ sufficient fluoride salt to release about 300 ppm to about 2,000 ppm, or about 800 ppm to about 1,500 ppm, of fluoride ion.

In certain embodiments, the dental care preparation includes a zinc salt, such as zinc lactate. The zinc salt may total from about 0.05% to about 10%, from about 0.1% to about 5% or from about 0.8% to about 3% by weight of the oral composition.

The dental care preparation may contain an orally acceptable vehicle, such as a humectant which may be, e.g., glycerine or sorbitol or an alkylene glycol such as polyethylene glycol or propylene glycol. The vehicle may total about 20% to about 75% by weight of the oral composition or about 25% to about 60% by weight.

The dental care preparation may contain a dentally acceptable abrasive material such as sodium bicarbonate or water insoluble abrasive material such as sodium metaphosphate, potassium metaphosphate, tricalcium phosphate, dihydrated dicalcium phosphate, anhydrous dicalcium phosphate, calcium pyrophosphate, calcium carbonate, aluminum silicate, hydrated alumina, calcined alumina, silica, bentonite, or any combination thereof.

The abrasive material may generally be present in the paste or gel composition in weight concentrations of about 10% to about 60% by weight. In further embodiments the weight concentrations may be about 10% to about 30% in a gel or about 25% to about 60% in a paste.

Additionally, crystalline or powdered N-methylol transfer agent may act as an abrasive, and residual crystalline or powdered N-methylol transfer remaining in the mouth after brushing retains antimicrobial activity after brushing.

Toothpastes as well as gel dentifrices typically contain a natural or synthetic thickener or gelling agent in proportions of about 0.1% to about 10% by weight or about 0.5% to about 5% by weight. Suitable thickeners or gelling agents include, e.g., Irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose and sodium carboxymethyl cellulose.

In certain embodiments, the dental preparation may contain a suitable amount of pH control. The pH control may be, e.g., sodium hydroxide.

Any suitable hydrating agents may also be employed to the dental care preparation. Such hydrating agents may include, e.g., glycerin, polyethylene glycol, paraffin oil, or any combination thereof.

The dental care preparation may further contain a coloring agent such as titanium dioxide.

Any suitable flavoring or sweetening material may also be employed. Examples of suitable flavoring constituents include, e.g., flavoring oils, e.g. oil of spearmint, peppermint, wintergreen, sassafras, clove, sage, eucalyptus, cinnamon, lemon, and orange, and methyl salicylate. Suitable sweetening agents include sucrose, lactose, maltose, xylitol, sodium cyclamate, perillartine, aspartyl phenyl alanine methyl ester, saccharine and the like. Suitably, flavor and sweetening agents may each or together, e.g., comprise from about 0.1% to about 5% or more of the preparation.

The dental care preparation may contain a binding agent. The binding agent may be, e.g., polyvinylmethyl ether maleic acid copolymer.

Agents used to diminish teeth sensitivity such as strontium chloride, potassium nitrate and potassium citrate may also be included in the dental care preparation of the present disclosure at concentrations of, e.g., about 0.1% to about 10% by weight.

Various other materials may be incorporated in the oral compositions of this disclosure including whitening agents such as urea peroxide, hydrogen peroxide, preservatives, such as sodium benzoate, vitamins and chlorophyll compounds. These adjuvants, when present, are incorporated in the compositions in amounts which do not substantially adversely affect the properties and characteristics desired.

The dental care preparation of the present disclosure may be prepared by suitably mixing the ingredients. For instance, in the preparation of a toothpaste, the N-methylol transfer agent is dispersed in a mixture of ingredients, e.g. humectants, surfactants, binding agents, a thickening agent, a pH control and salts such as sodium fluoride and flavor may then be added and mixed. The ingredients may then be mixed under vacuum for about 15-30 minutes. The resulting toothpaste product is then packaged. In certain embodiments, the N-methylol transfer agent is dissolved in the preparation. In further embodiments, the N-methylol transfer agent is dispersed in the preparation in microcrystalline, crystalline, and/or powder form.

EXAMPLE

The antimicrobial effect of fluorides against oral bacteria associated with dental caries and periodontal disease has been tested both in-vitro and in-vivo. Respective bacteria of the oral cavity include *Streptococcus mutans, Streptococcus sanguis, Streptococcus salivarius, Actinomyces viscosus*, and lactobacilli and others. Antimicrobial susceptibility testing (antibiogram) procedure is performed in a manner similar to that of conventional antibiotics by agar dilution technique, but the MIC values sometimes are given in ppm F (parts per million, 1 ppm=$10^{-6}$). In a paper by MANDELL R. L. (Sodium fluoride susceptibilities of suspected periodotopathic bacteria, J. Dent. Res. 62 (6): 706-708 (1983)) the MIC values for 25 strains are given in mg/ml as is usual for antibiotics.

As can be seen, these values are two orders of magnitude higher than with conventional antibiotics. However commercial fluoride preparations can deliver fluoride ion concentrations to the tooth ranging from 225 µg/ml to 12,300 µg/ml which can be achieved with the commonly used toothpastes. Different fluoride compounds have different bactericidal effects against oral microorganisms. The metal fluoride salts $CuF_2$ and $SnF_2$ for instance are more bactericidal than NaF or $NH_4F$.

Investigations have shown that the maximum time of exposure of dental preparations in use is several minutes. It is therefore desirable to have a toothpaste formulation with the longest possible exposure time.

As with conventional antibiotics there may occur microbial resistance problems with fluoride. There have been reports about in vitro adaptation of oral streptococci to inhibitory level of fluoride. The ability of some strains of streptococci to achieve fluoride tolerance also may develop during prolonged topical fluoride use.

It therefore is advantageous to have a toothpaste with taurolidine and/or tauraltam in combination with metal fluoride salt in view of the lack of antibiotic resistance observed with taurolidine against conventional antibiotics, also achieved with fluor-ion resistant bacteria. There unexpectedly also is no interaction between taurolidine and fluorides. A mutual potentiation of the effect and a prolongation of exposure time is further advantageous.

The invention claimed is:

1. A dental care preparation in a form of a toothpaste or tooth gel dentifrice comprising an antimicrobial amount of at least one antimicrobial N-methylol transfer agent, and at least one of a fluoride compound or a source of fluoride ions, wherein said N-methylol transfer agent is taurolidine, taurultam, or a combination thereof.

2. The dental care preparation of claim 1, wherein at least a portion of said N-methylol transfer agent is dissolved in said preparation.

3. The dental care preparation of claim 1, wherein at least a portion of said N-methylol transfer agent is dispersed in said preparation as at least one of a microcrystalline, a crystalline, or a powder form.

4. The dental care preparation of claim 2, wherein at least a portion of said N-methylol transfer agent is further dispersed in said preparation as at least one of a microcrystalline, a crystalline, or a powder form.

5. The dental care preparation of claim 1 wherein at least a portion of said agent is in microcrystalline, crystalline or powder form.

6. The dental care preparation of claim 5 wherein the microcrystalline, crystalline or powder form agent functions as an abrasive in said preparation.

7. The dental care preparation of claim 1, comprising about 0.01-10% by weight said N-methylol transfer agent.

8. The dental care preparation of claim 1, comprising about 0.1-5% by weight said N-methylol transfer agent.

9. The dental care preparation of claim 1, comprising about 1-2% by weight said N-methylol transfer agent.

10. The dental care preparation of claim 1, comprising about 2% by weight N-methylol transfer agent.

11. The dental care preparation of claim 1, comprising about 3% by weight said N-methylol transfer agent.

12. The dental care preparation of claim 1, comprising about 0.0005-3% by weight said fluoride compound or source of fluoride ions.

13. The dental care preparation of claim 1, comprising about 300-2,000 ppm fluoride ion.

14. The dental care preparation of claim 1, further comprising a zinc salt.

15. The dental care preparation of claim 14, wherein said zinc salt is zinc lactate.

16. The dental care preparation of claim 14, comprising about 0.05% to about 10% by weight of said zinc salt.

17. The dental care preparation of claim 1, further comprising, at least one of a thickening agent, a pH control agent, a humectant, a sweetener agent, a binding agent, a hydrating agent, a coloring agent, and a surfactant.

18. The dental care preparation of claim 14, wherein said thickening agent is selected from the group consisting of Irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose, and sodium carboxymethyl cellulose, said pH control agent comprises sodium hydroxide; said humectant is selected from the group consisting of glycerine, sorbitol, an alkylene glycol, and any combination thereof; said sweetener agent is selected from the group consisting of sucrose, lactose, maltose, sylitol, sodium cyclamate, perillartine, aspartyl phenyl alanine methyl ester, saccharine, and any combination thereof; said binding agent comprises polyvinylmethyl ether maleic acid copolymer; said hydrating agent is selected from the group consisting of glycerin, polyethylene glycol, paraffin oil, and any combination thereof; said coloring agent comprises titanium dioxide; and said surfactant is selected from the group consisting of sodium lauryl sulfate, sodium lauryl sarcoside, sodium monoglyceride sulfate, and any combination thereof.

* * * * *